United States Patent
McDonnell et al.

(10) Patent No.: US 8,673,212 B2
(45) Date of Patent: Mar. 18, 2014

(54) APPARATUS TO DECONTAMINATE EQUIPMENT CONTAINING INTERNAL CHANNELS

(75) Inventors: Gerald McDonnell, Hampshire (GB); Andy Witschi, Nidau (CH)

(73) Assignee: Steris Corporation, Mentor, OH (US)

( * ) Notice: Subject to any disclaimer, the term of this patent is extended or adjusted under 35 U.S.C. 154(b) by 245 days.

(21) Appl. No.: 13/068,986

(22) Filed: May 25, 2011

(65) Prior Publication Data

US 2011/0290034 A1 Dec. 1, 2011

Related U.S. Application Data

(60) Provisional application No. 61/396,533, filed on May 28, 2010.

(51) Int. Cl.
*A61L 2/24* (2006.01)
*A61L 2/18* (2006.01)
*A61L 2/20* (2006.01)

(52) U.S. Cl.
USPC .............................................. 422/28; 73/40

(58) Field of Classification Search
USPC .............................................. 73/40; 422/28
See application file for complete search history.

(56) References Cited

U.S. PATENT DOCUMENTS

| | | | |
|---|---|---|---|
| 4,548,197 A * | 10/1985 | Kinoshita ...................... | 600/158 |
| 4,721,123 A | 1/1988 | Cosentino et al. | |
| 5,236,673 A * | 8/1993 | Coakley et al. .......... | 422/186.07 |
| 5,279,799 A | 1/1994 | Moser | |
| 5,310,524 A | 5/1994 | Campbell et al. | |
| 5,492,672 A * | 2/1996 | Childers et al. ................. | 422/28 |
| 5,858,305 A | 1/1999 | Malchesky | |
| 6,047,431 A * | 4/2000 | Canonica ................. | 15/104.095 |
| 6,408,682 B2 * | 6/2002 | Greszler ............................ | 73/40 |
| 6,485,684 B1 * | 11/2002 | Mapson et al. ................. | 422/28 |
| 6,814,932 B2 | 11/2004 | Hlebovy et al. | |
| 6,884,392 B2 | 4/2005 | Malkin et al. | |
| 6,915,810 B2 | 7/2005 | Weber | |
| 7,479,257 B2 | 1/2009 | Nguyen et al. | |
| 7,901,349 B2 * | 3/2011 | Feld et al. ..................... | 600/155 |
| 2002/0131913 A1 * | 9/2002 | Tamata et al. ................. | 422/171 |
| 2005/0079094 A1 * | 4/2005 | Mariotti et al. .................... | 422/3 |
| 2005/0148819 A1 * | 7/2005 | Noguchi et al. ............. | 600/133 |
| 2007/0193605 A1 * | 8/2007 | Kuroshima et al. ............. | 134/18 |
| 2008/0038096 A1 * | 2/2008 | Fausto et al. ................... | 414/217 |
| 2008/0166264 A1 * | 7/2008 | Halstead et al. ................ | 422/29 |
| 2009/0044845 A1 | 2/2009 | Cui et al. | |

* cited by examiner

*Primary Examiner* — Lisa Caputo
*Assistant Examiner* — Punam Roy
(74) *Attorney, Agent, or Firm* — Hudak, Shunk & Farine Co., LPA

(57) ABSTRACT

A self contained unit and system for determining whether medical equipment or devices such as endoscopes, minimally invasive surgical instruments (MIS), etc., are blocked, or substantially free flowing, or are disconnected or leaking before they are subjected to cleaning and/or a disinfecting process that is either sequential or simultaneous. The apparatus has a manifold that generally receives predetermined amounts of a gas and/or liquid for dispensing to one and preferably a plurality of channels. Advantageously, the test apparatus of the present invention can be utilized as a stand-alone unit that is able to monitor the noted medical equipment or devices with regard to the flow of a gas and/or liquid therethrough such as large or small lumens and such flow can also be automatically verified by a system independent of human intervention. Alternatively, the test apparatus can be utilized as part of a comprehensive system in conjunction with other devices for testing, cleaning, and/or disinfecting.

19 Claims, 6 Drawing Sheets

APPARATUS TO DECONTAMINATE EQUIPMENT CONTAINING INTERNAL CHANNELS

CROSS-REFERENCE

This application claims the priority filing date of U.S. Provisional Application Ser. No. 61/396,533 filed May 28, 2010, herein fully incorporated by reference.

FIELD OF THE INVENTION

The test apparatus of the present invention is a self contained unit and system for determining whether medical equipment or devices such as endoscopes, minimally invasive surgical instruments (MIS), etc., are blocked, or substantially free flowing, or are disconnected or leaking before they are subjected to cleaning and/or a disinfecting process that is either sequential or simultaneous. The apparatus has a manifold that generally receives predetermined amounts of a gas and/or liquid for dispensing to one and preferably a plurality of channels. Advantageously, the test apparatus of the present invention can be utilized as a stand-alone unit that is able to monitor the noted medical equipment or devices with regard to the flow of a gas and/or liquid therethrough such as large or small lumens and such flow can also be automatically verified by a system independent of human intervention. Alternatively, the test apparatus can be utilized as part of a comprehensive system in conjunction with other devices for testing, cleaning, and/or disinfecting.

BACKGROUND OF THE INVENTION

Reusable channel containing medical devices such as endoscopes, and minimally invasive devices, are widely used for a variety of non-invasive and invasive surgical procedures and are noted as being difficult to decontaminate due to lack of sufficient penetration of gas or liquid through their entire length and lack of sufficient contact times. Of particular concern are blockages of such narrow devices, due to the buildup or deposition of soil that will impede the flow of liquid and gases, or leakage as caused by connection of the devices that can often go unnoticed by users and staff.

U.S. Pat. No. 5,279,799 relates to an apparatus for cleaning and testing endoscopes by injecting pressurized air into the sheath and pressurized air and washing liquid into the ducts, and monitoring the same. A washing chamber is provided which contains retractable cages to hold the endoscopes during cleaning and testing. The cages include a coupler for detachably connecting tubes supplying the air and washing liquid to the endoscopes. The cages also have markings for automatically activating the apparatus when a cage containing an endoscope is inserted into the washing chamber. The apparatus further requires a tight attachment of a connector to the said lumen to allow for the flow of air. With these connectors, there is a risk of occlusion of material at the contact sites, which do not allow for adequate contact with cleaning and disinfection chemistries during the decontamination process.

Some cleaning and/or disinfection systems utilize connectors that can have leakage around contact points, but the detection of adequate flow is often difficult. Other systems describe using liquid under pressure to permit flow through lumens of medical devices in the absence of any connectors, but likewise they cannot ensure that all lumens are free-flowing.

SUMMARY OF THE INVENTION

An independent or integral apparatus for screening, testing, and monitoring various channel-containing medical devices comprises a hollow manifold for receiving fluids such as air and/or liquid such as water, cleaning solutions, and the like. The manifold has a plurality of connectors for attachment to a multiplicity of devices to be tested and has one or more pressure sensors for determining whether a particular device is generally blocked, leaking or open thereby permitting the free flow of fluids therethrough. One or more solenoids control the flow of the manifold fluid either sequentially or simultaneously to one or more devices.

In one embodiment, the test apparatus is designed to determine if a blockage is present in a channel of a medical device, or whether the device contains a leak, and can also perform a cleaning operation on the device. Tests of multiple medical devices can be performed sequentially or simultaneously. An advantage of the present invention is that the test apparatus is able to ensure the flow of a gas and/or liquid to any channel diameter size.

In one embodiment, an integral apparatus for testing and/or cleaning a channel containing medical device, comprises a hollow manifold having at least one connector, said manifold having at least one pressure sensor for determining the pressure therein, and a solenoid valve operatively connected to said connector and capable of being operatively connected to said channel containing medical device; an airflow line having a pressure switch and a solenoid valve, said airflow line capable of maintaining a predetermined pressure, said airflow line connected to said manifold; a microprocessor operatively connected to said airflow line pressure switch, said microprocessor also being operatively connected to said manifold pressure sensor and operatively connected to said airflow line solenoid valve, and said microprocessor, upon receiving a signal from said manifold pressure sensor detecting a pressure in said manifold, being capable of energizing said airflow line solenoid valve and also opening said solenoid valve connected to said connector so that said air in said manifold is capable of flowing into said channel containing medical device.

In a further embodiment, a method for testing a channel containing medical device, comprises the steps of obtaining a testing apparatus comprising a hollow manifold having at least one connector, a solenoid valve operatively attached to said connector and capable of being attached to a channel containing medical device, said manifold having at least one pressure sensor for determining pressure within the manifold, said apparatus further including an airflow line having a pressure switch and an airflow line solenoid valve, said airflow line operatively connected to said manifold, said testing apparatus further including a microprocessor operatively connected to said pressure switch of said airflow line, to said airflow line solenoid valve, to said manifold pressure sensor, and to said connector solenoid valve; operatively connecting said connector solenoid valve to said channel containing medical device; and opening said airflow solenoid valve and determining the pressure in said manifold with said manifold pressure sensor.

BRIEF DESCRIPTION OF THE DRAWINGS

The present invention will be better understood by reference to the following drawings wherein.

DETAILED DESCRIPTION OF THE INVENTION

While the present invention relates to test apparatuses for medical equipment or devices having internal channels such as endoscopes, dental equipment, minimally invasive surgical instruments, etc., it will generally be described with regard to a preferred embodiment, i.e. a device containing a lumen. The test apparatus is suitable for use in a variety of applications or environments. In one embodiment, the test apparatus can be utilized as a stand-alone device at any desired location such as in relatively close proximity to a sink or drain. In a further embodiment, the test apparatus can be utilized in conjunction with one or more additional devices or processes or combinations thereof. For example, the test apparatus can be utilized with or in the device described in U.S. Pat. No. 5,279,799, fully incorporated herein by reference. The test apparatus can be utilized to check one or more medical devices having an internal channel for blockage, leakage, or as a cleaning or disinfection apparatus, or a combination thereof.

Figure 1:
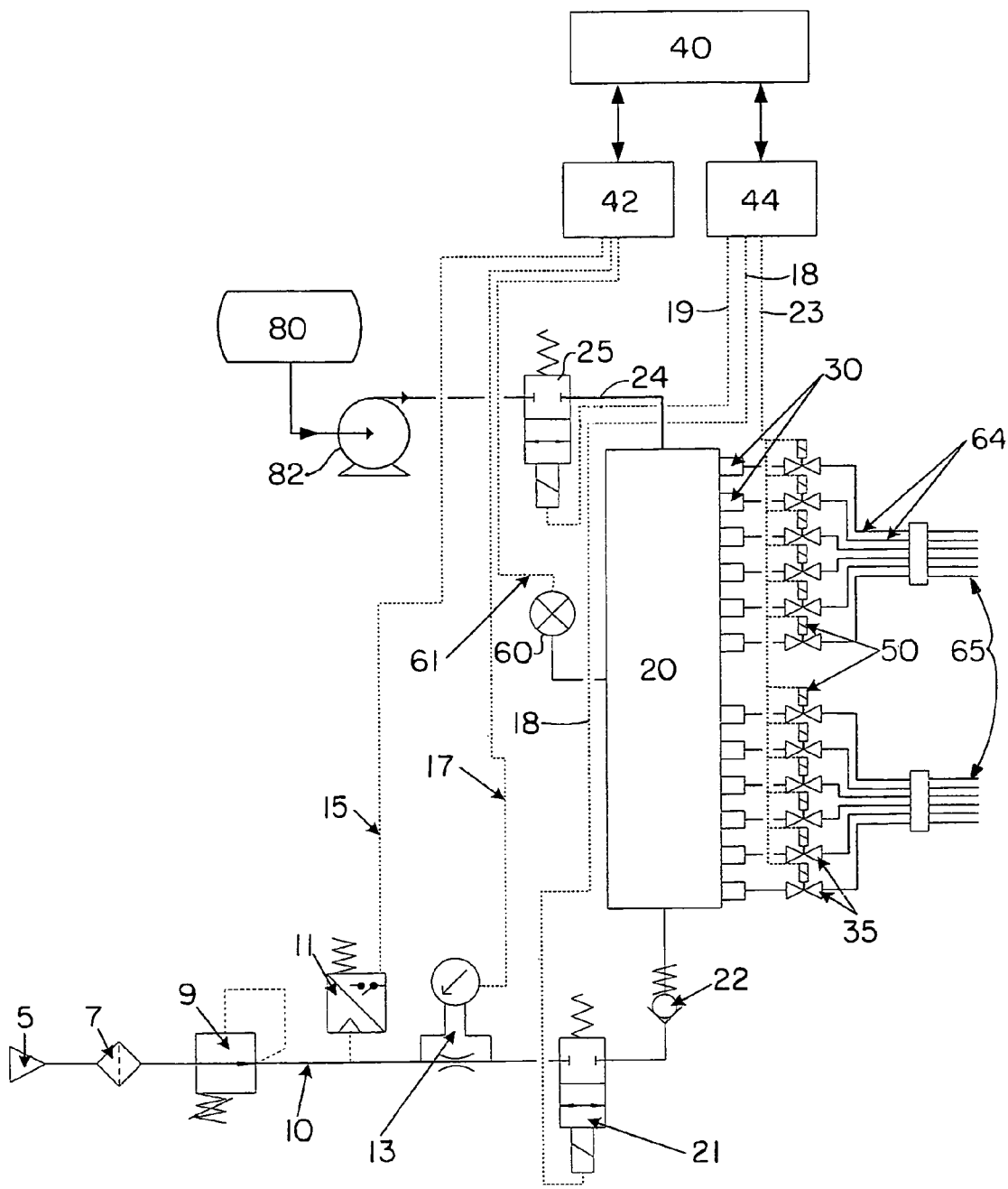
FIG. 1 is a schematic view showing a test apparatus for a channel containing medical device wherein a plurality of connectors, contained on a manifold, are each operatively connected to a solenoid valve assembly for controlling the amount of fluid emitted from the manifold and into the medical device.
Figure 2:
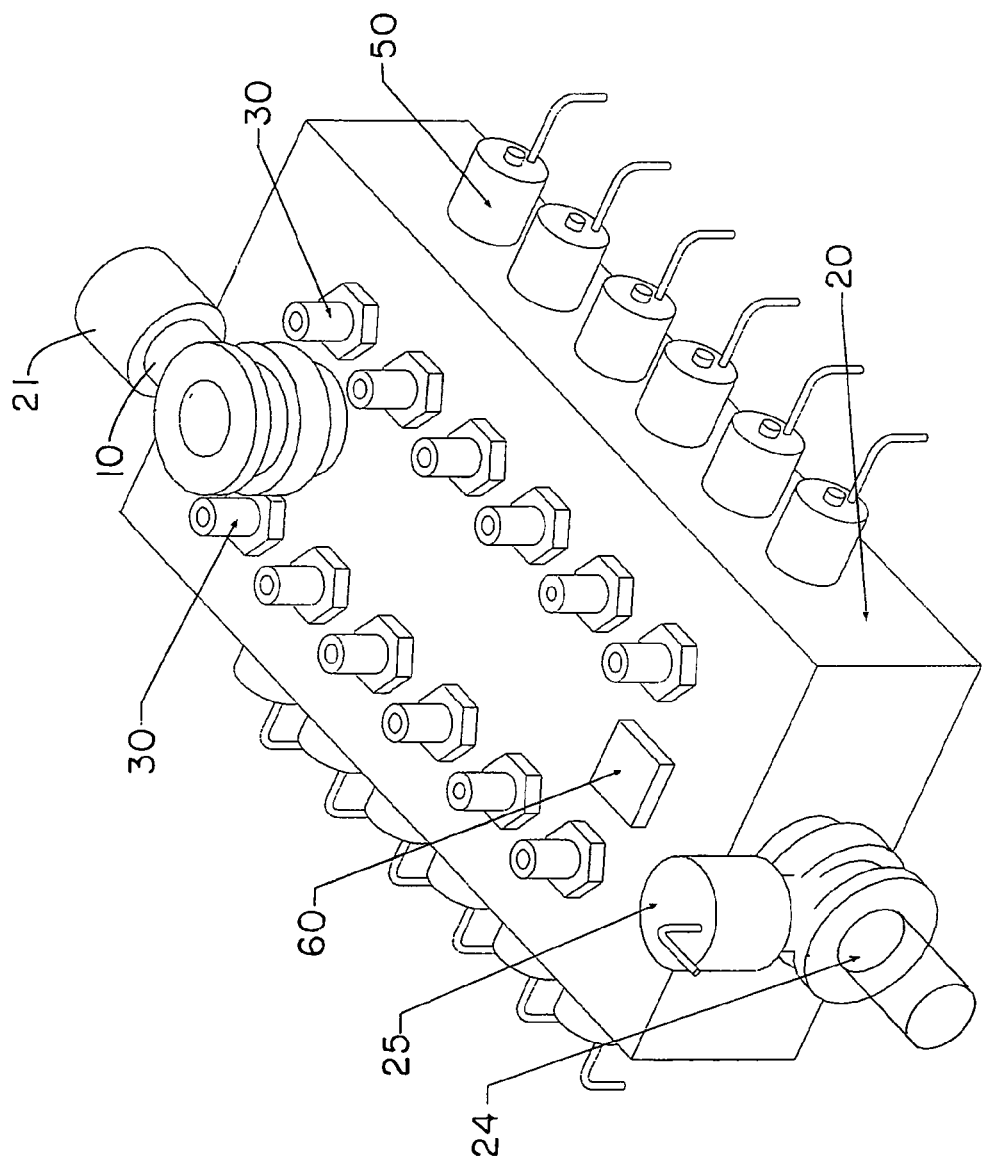
FIG. 2 is a perspective view of the connector manifold of FIG. 1.

The test apparatus of the present invention ensures that channel containing devices are suitable (e.g. unblocked and not leaking) for subsequent cleaning, disinfection, sterilization, or any combination thereof. An embodiment of such a test apparatus 1 is shown in FIGS. 1 and 2, and comprises manifold 20. The manifold receives a fluid, for example, a gas such as air or a liquid such as water and the same is admitted to manifold 20 at a predetermined pressure generally determined by the maker of the medical equipment or device, for example an endoscope, etc. The pressure within the manifold is generally from about 500 or about 600 millibars (0.05 to 0.06 MPa) to about 1,000 or about 2,000 or about 5,000 millibars (0.1 or 0.2 or 0.5 MPa). The embodiments of FIGS. 1 and 2 will be first discussed with respect to an air input, then initialization of the test, followed by a description of the test with respect to a channel containing device.

Manifold 20 generally contains a hollow portion or chamber wherein the liquid (e.g. water) or a gas (e.g. air) or any combination thereof, resides until needed. For example, manifold 20 can contain from about 1% or about 10% to about 90% or about 99% by volume of air with the remaining being the liquid. In a preferred embodiment, preferably either only air or only water is utilized, or if a cleansing fluid is desired, air and water containing a cleansing surfactant can be alternately transferred through manifold 20 to provide a pulsing effect. Manifold 20 can be drained at the end of a test cycle.

FIG. 1 is a representation of various functional elements of the apparatus and a process emphasizing an order of the elements and FIG. 2 sets forth an example of a specific mechanical design.

Air Input

Integral test apparatus 1 contains compressed air source 5 that generates air pressure as limited by pressure regulator 9, to a certain preselected value such as about 1 bar (0.1 MPa) within manifold 20. Downstream solenoid 21 is normally maintained in a closed position during the initial compression of the air. Filter 7 is utilized to clean the air. The presence of a working pressure is confirmed by pressure switch 11 that constantly monitors the pressure and sends a signal through electrically conductive line 15 that is connected to input module 42 of control unit or microprocessor 40. When the testing apparatus is in use, the loss of the electrical signal (i.e. no signal) to the input module, as caused by the pressure dropping below a predetermined value, results in a response, for example termination of a flow of compressed air and a display of a warning signal such as a visual signal, or an audible alert, etc. by the microprocessor 40.

Initialization of Test Apparatus 1

The test procedure is initiated in any number of ways such as by pressing a button that is electronically connected to input module 42, by powering up the device, or desirably by touching a screen of a display such as a color liquid crystal display, so that control unit 40 activates output module 44 that energizes solenoid valve 21 through electrically conductive line 18. Valve 21 is generally closed if not activated or energized. Once energized, compressed air flows through pressure regulator 9, past pressure switch 11 and through a flow mechanism such as an orifice, a Venturi tube, or a flow nozzle, embodied in airflow measuring device 13, and through the open solenoid valve 21. The compressed air then fills hollow manifold 20 to a desired, preselected pressure as well as tubes or lines located between manifold 20 and the plurality of solenoid values 35. Depending upon the design of the test apparatus, valves 35 can either be opened, but preferably are not activated or energized and thus are normally closed thereby impeding the flow of the compressed air. The amount of pressure in the manifold is theoretically equal to the pressure determined by pressure regulator 9. However, in reality it is generally lower, such as from about 0.1 to about 0.2 bars (0.01 to 0.02 MPa) lower, because of check valve 22.

The primary purpose of check valve 22 is to prevent any backflow, especially when the device is in the washing phase. That is, in the embodiment shown in FIG. 1, the manifold 20 is shared by the testing apparatus containing compressed air as well as a washing fluid. Thus, depending upon the stage of utilization of the testing apparatus, manifold 20 can be filled with air, or be filled with water, for example hot or cold, with or without detergent, etc. Wash chamber reservoir 80, pump or motor 82, and upper solenoid valve 25 activated by output module 44 through electrically conductive line 19, are utilized preferably with regard, to the washing cycle. Thus, check valve 22 serves to protect any instrumentation between compressed air source 5 and check valve 22.

As shown in FIGS. 1 and 2, connectors 30 extend outwardly from the manifold and can have ribs thereon, not shown. In lieu of ribs, any other suitable fastening device such as a clamp or external fastening band can be utilized. Each connector 30 is connected to an individual solenoid valve 35 having an on-off or open and closed position therein to admit the compressed air through the manifold and through an individual connector 30 to a channel containing device. Each connector 30 can be directly attached to a channel containing device or through a conduit, e.g. tube 67, that can have a wide range of internal diameters and also different wall thicknesses, to the channel containing device.

Pressure sensor 60 of FIG. 1 measures the actual pressure inside manifold 20 and transduces the pressure value into an electrical signal carried through electrical line 61 that is then read by input module 42 of control unit 40.

At this phase of the operation, the test apparatus can perform a self test. That is, if the value of pressure read by pressure sensor 60 is much lower than the expected pressure, for example about 0.9 bar (0.09 MPa), the same indicates a malfunction somewhere in the system such as the compressed air source 5, pressure regulator 9, any of valves 35, etc., or a loss of electrical connection between pressure sensor 60 and input module 42, and the like. During initialization of the test, the pressure difference directly before and after airflow measuring device 13 is measured. Since there is a relation between the flow value and the value of the differential pressure of device 13, the value of the airflow can be readily determined. This value is then transduced into an electrical signal that flows through electrically conductive line 17 that is then read by input module 42 of control unit 40. After the transitional phase of filling the testing apparatus, and especially manifold 20, the airflow value should be zero. If not, then the same is an indication that there is leakage in the system or some of the valves 35, etc., are not properly closed. Control unit 40 compares the pressure and flow values to determine the airflow value.

Flow Test of Individual Channel Containing Devices

After the manifold is filled with compressed air and an optional self-test has been completed, i.e. and it is determined that there is no leakage in the system, etc., a control is activated that through electrically conductive line 23 energizes a specific solenoid 50 that opens a preselected valve 35 of the many valves shown in FIG. 1. Airflow line solenoid 21 is also energized or opened. The compressed air can then freely flow from air source 5 through flow line 10 into manifold 20 and then into the opened predetermined solenoid valve 35 and into a channel containing medical device 65 such as an endoscope attached via connection line 64 to the open valve. The airflow and the pressure maintained inside the manifold are influenced by the diameter and length of the channel containing device being tested. Once the transitional phase of transferring compressed air into the channel containing device has stabilized, e.g. a constant pressure value is maintained, the flow value of device 13 is read by control unit 40 and compared with a value that is stored within an internal memory of control unit 40. Such stored values of airflow and/or pressure can be readily determined in a manner known to the art and to the literature, with regard to various different sized channel containing devices, diameters, and the like. If the airflow value of device 13 is similar to the predetermined value, a channel containing device is considered to be open or clear. If the value is lower than the predetermined value, the channel containing device is then generally considered to be blocked. If blocked, the channel containing device is removed and maintenance thereon is conducted to remove the blocking material. If the airflow value is higher than the predetermined airflow value for the channel containing device, the same generally indicates that there is either not a proper air-tight connection between the channel containing device and the open valve, or that the channel containing device may be leaking. In such a situation, naturally the cause of the excessive flow rate is determined and repaired.

An alternative procedure to determine the airflow through the channel containing device is to utilize pressure sensor 60 located on manifold 20 as shown in FIG. 2. The value of the pressure determined by pressure sensor 60 can be compared to the predetermined control unit value, or the pressure value from sensor 60 can be combined with the airflow value of device 13 using a mathematical formula to determine a suitable pressure within a particular channel containing device being tested. If the value of the pressure within manifold 20 is above a predetermined value, i.e. generally equal to the pressure permitted by pressure regulator 9, the channel containing device is blocked. If the pressure is lower, then either the channel is leaking, and/or there is a leak in the connection between the channel containing device and the open valve. If the pressure is relatively equal to the calculated pressure, the channel containing device is clear.

Once a particular channel containing device has been tested as indicated above, it can be removed with the particular individual solenoid 50 closing its respective internal valve 35 (not shown). The procedure is then repeated with respect to other channel containing devices attached to other solenoid valves 35 that are controlled by their respective solenoids 50.

The testing apparatus of FIGS. 1 and 2 is designed generally to test one channel containing medical device at a time. Thus, once the test is finished, a second channel containing device can then be immediately tested as well as the remaining channel containing devices in quick succession. During the course of testing the subsequent channel containing device, the previously tested channel containing devices can be removed and a new channel containing device attached thereto for testing.

While the invention has been described with regard to channel containing devices, it is to be understood that any type of tube, conduit, hose, endoscope, etc. having a wide range of internal diameters and also of different wall thicknesses can be tested with regard to blockage, and the like.

Once testing is completed, if so desired, the various channel containing devices, conduits, can be subsequently washed. Washing is readily obtained by pumping a washing fluid, for example water and a detergent, from wash chamber reservoir 80 via pump or motor 82 through solenoid valve 25 located on connection line 24 that is in the open position into manifold 20 and subsequently into the various channel containing devices upon the opening of individual valves 35 upon a signal from its respective individual solenoid 50. Due to the existence of check valve 22, the wash fluid will not enter into the compressed air source line 10.

While the invention has been described with regard to the specifically above-noted pressure, any amount of pressure can be utilized to be admitted to a particular conduit, tube, and the like. For example, as noted above, pressure can range from about 1 bar (0.1 MPa) to about 5 bars (0.5 MPa) and desirably from about 1 bar (0.1 MPa) to about 2 bars (0.2 MPa).

It is an aspect of the present invention that the various pressure readings or airflow readings as determined by pressure sensor 60 or airflow mechanism 13 can be determined visually, i.e. by simply reading a gauge or by an audible signal such as a buzzer or alarm, etc, that is calibrated to activate upon exceeding a preselected or predetermined fluid pressure value or range, or by falling below such an indicated suitable range, or preferably both. Since, as noted, manifold 20 is connected to every individual connector 30 and to every valve 35, each medical device such as an endoscope connected to each solenoid can be sequentially tested. Depending upon the medical device being tested, different limits with regard to unsuitable or undesired high pressure as well as low pressure readings can be set and such limits can vary from device to device. Thus, for one device, an unsuitable pressure reading can vary from greater than or less than 10% of a selected value and with respect to another device it can vary from greater than or less than 15% of a desired pressure value and so forth. If a channel containing device is partially or totally blocked, it can be cleaned in a manner as noted above or can be cleaned as by subjecting it to a series of pulses or blasts of water, or air, or combinations thereof.

Figure 3:
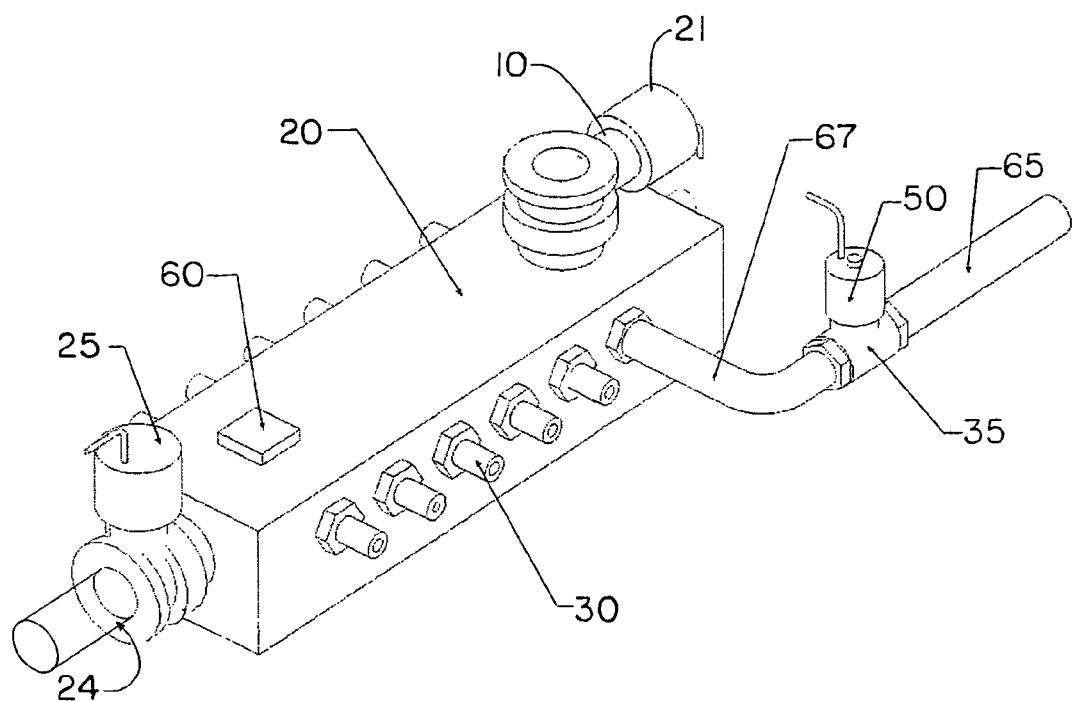
FIG. 3 is a perspective view of a further embodiment of a test apparatus wherein the solenoid valve is external of the manifold.

FIG. 3 is similar to FIG. 2 and shows an example of a manifold 20 having pressure sensor 60 thereon as well as an input line having check valve 22 thereon. Unlike FIG. 2 which has valves 35 integral with the manifold 20 and connectors 30 are connected to a channel containing device (not shown), the embodiment of FIG. 3 has external valves 35 and solenoids 50 that are connected to the manifold block via a connecting tube 67. For sake of clarity, while only one such connecting tube is shown connected to channel containing device 65, it is to be understood that all connectors 30 can have a connecting tube 67 thereon, each connected to a different channel containing device 65. The manifold block of FIG. 3 is similar to that of FIGS. 1 and 2 and is thus connected in the same manner with respect to all the connection lines, control unit 40 having input module 42 and output module 44, and the various devices or elements contained on air input line 10 as set forth in FIG. 1. Of course, the mode of operation and testing of the individual channel containing devices and all other aspects is the same and is not repeated but hereby fully incorporated by reference with respect to FIGS. 1 and 2.

Figure 4:
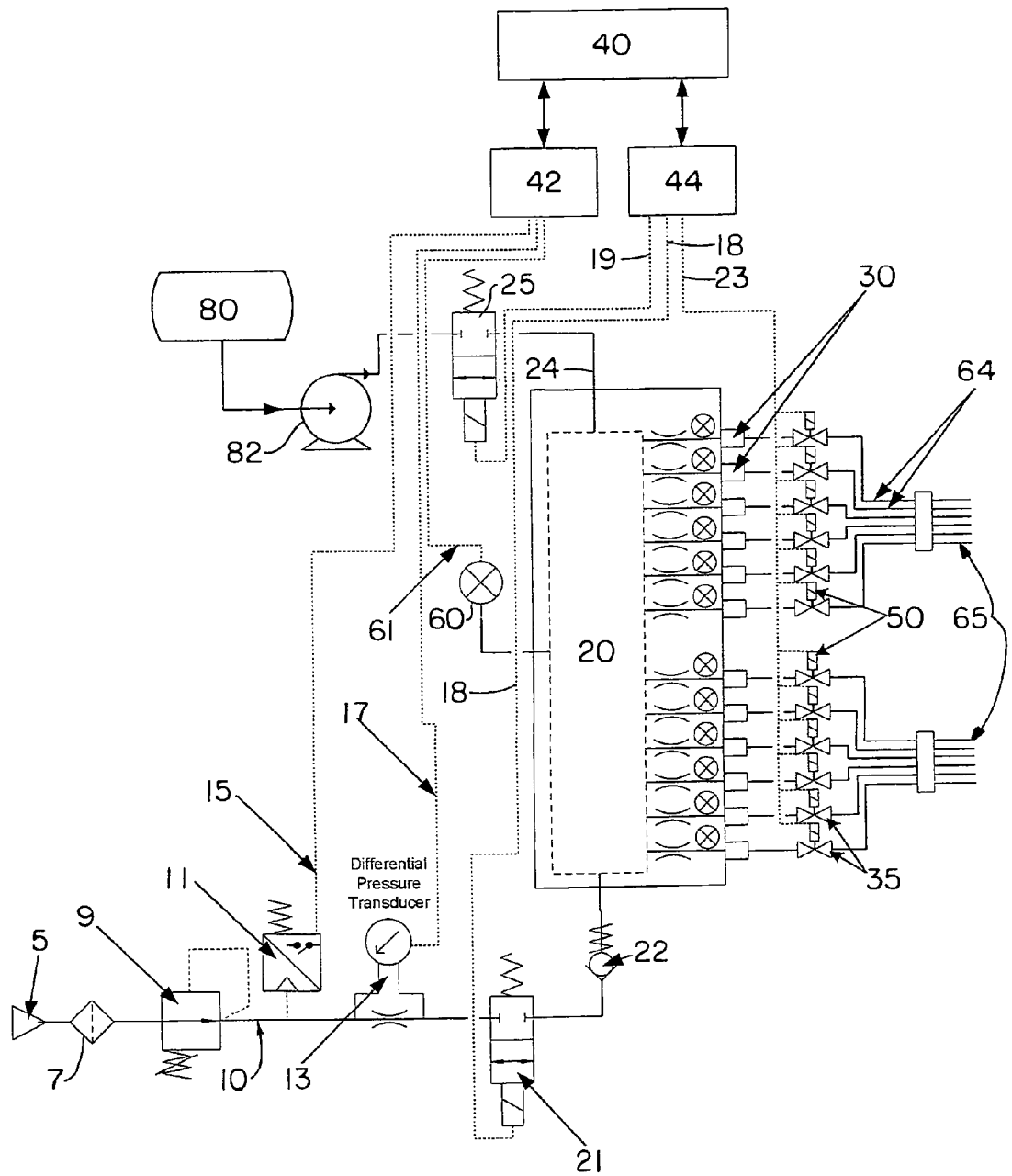
FIG. 4 is a schematic view of another embodiment of a test apparatus for a channel containing medical device similar to FIG. 1 wherein each connector has a pressure sensor.
Figure 5:
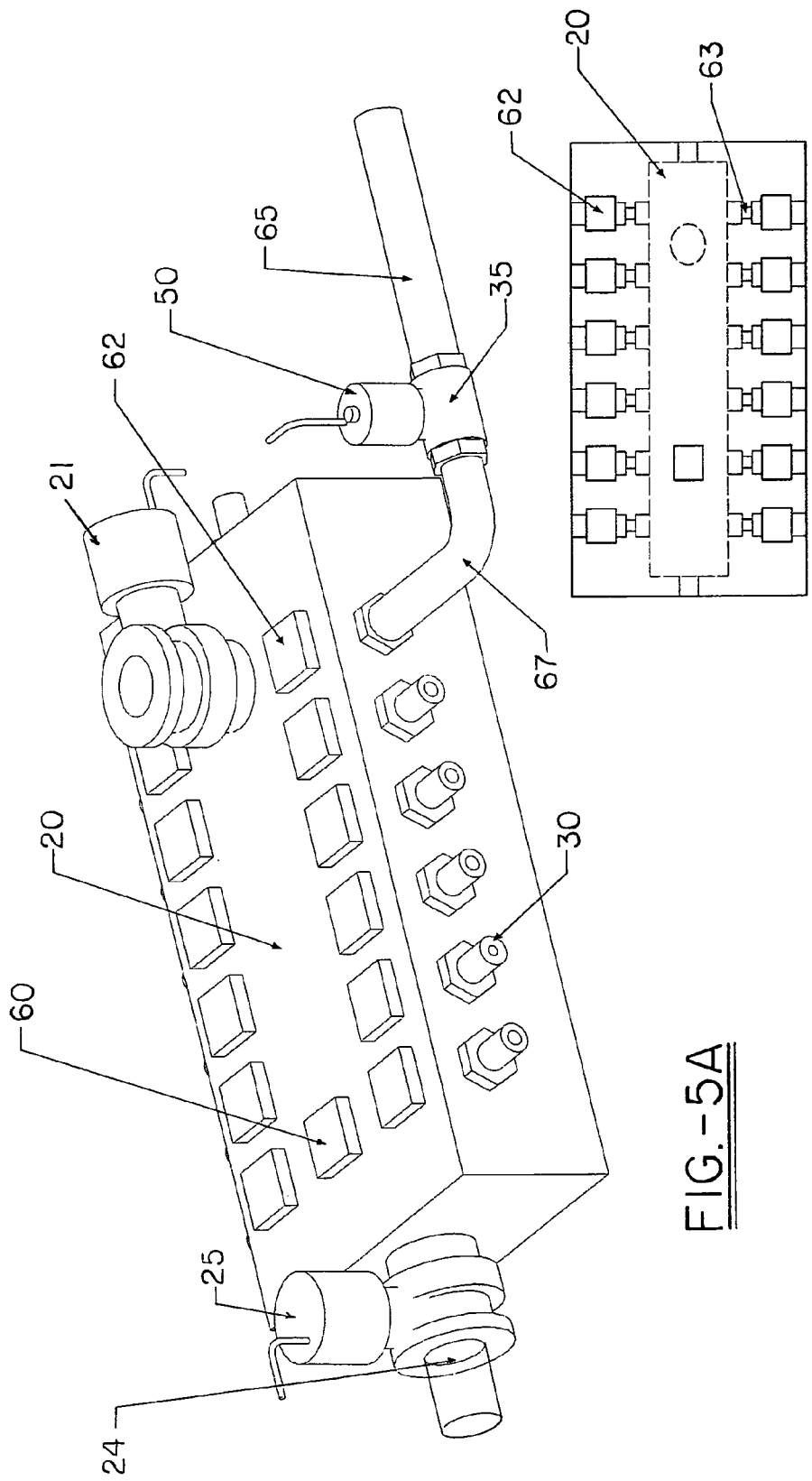
FIG. 5A is a perspective view of the test apparatus embodiment of FIG. 4.
FIG. 5B is a top plan view of FIG. 5A showing manifold 20 and individual side channel pressure sensors 62.

Another embodiment of the present invention as set forth in FIGS. 4, 5A and 5B is essentially identical to that set forth in FIGS. 1 and 2 and hence will not be repeated but is hereby fully incorporated by reference. Summarizing, the test apparatus of FIGS. 4, 5A and 5B, they contain the same air compressor source 5 and flow line 10 having the same devices such as pressure regulator 9, pressure switch 11, airflow measuring device 13, solenoid 21 and check valve 22 as in FIG. 1 along with the same connecting lines 15, 17, and 18 as in FIG. 1. The optional washing system comprising wash chamber reservoir 80, wash pump or motor 82, and solenoid valve 25 is also identical. Through the electrical lines data and information are transmitted to input module 42 or electronic control unit 40. Output module 44 of the control unit sends information such as a signal to individual solenoids 50 to open and close valves 35. As with FIG. 1, the embodiments of FIGS. 4, 5A and 5B relate to the operation of one individual solenoid and one corresponding individual valve to test an individual channel containing device separately while all remaining valves are closed. However, unlike the embodiments of FIGS. 1 and 2, embodiments of FIGS. 4, 5A and 5B contain additional pressure sensors 62 located within or on manifold block 20. That is, as shown in FIGS. 5A and 5B, pressure sensor 62 measures the actual pressure in side chambers 63 that extend from manifold 20 through manifold 20 to connectors 30. When all valves 35 are closed, the pressure of all individual pressure sensors 62 and manifold pressure sensor 60 should be equal.

The operation of testing an individual channel containing device, as noted, is the same as set forth hereinabove with respect to the embodiment of FIGS. 1 and 2. The pressures within manifold 20 and also side chamber 63 are measured respectively by pressure sensors 60 and 62. These pressure values are transformed into electrical signals that are passed by a connection to input module 42 and analyzed by control unit 40 which compares these values with a pre-calculated value for a particular size, shape, diameter, channel containing device, e.g. a lumen. As noted above, control unit 40 will determine whether the pressure through channel containing device 65 is normal, or high indicating a blockage, or low indicating a leak in the system. The net effect of additional pressure sensor 62 is that it serves as a backup and improves the quality of the test apparatus. Once a test on an individual channel containing device, conduit, tube, etc., is completed, a test on a subsequent channel containing device can be initiated.

A plurality of channel containing devices can be connected to manifold 20 as shown in FIG. 4. The embodiment of FIG. 5A is similar to that of FIG. 3 in that while only one connection tube 67 containing valve 35 and solenoid 50 thereon is shown connected to lumen 65, each of connectors 30 can also contain the same set-up. With respect to both FIGS. 4, 5A and 5B, once a channel containing device 65 has been tested, it is disconnected from the corresponding valve 35 and a different channel-containing device is connected to be tested.

The method for combining the use of pressure switch 11 with airflow sensor 13 will now be described. That is, the test apparatus can determine blockage in a channel containing medical device through utilization of flow sensor 13 and pressure sensor 60, desirably in combination with a mathematical algorithm. As noted above, the compressed air is fed through line 10 and through one of several valves 35 to an associated channel containing device. Verification of the status of an individual channel containing device 65 is accomplished by opening corresponding valve 35. After a specific delay time (needed to elapse so that the flow rate and pressure are stabilized) both the airflow and air pressure are actively measured by flow and pressure sensors 13 and 60. From these two parameters the flow coefficient ($C_V$) is calculated. The value of the coefficient is then directly compared to a previously determined range.

The flow coefficient is calculated according to the following mathematical formula:

$$C_v = \frac{BQ}{P^A}$$

where:
Q—airflow [liters/min]
P—air pressure [mbar]
A—An experimental based pressure/Flow coefficient (for a given detection system defined in this patent disclosure as PTX+A=0.6), and
B—Scale coefficient (for a given detection system defined in this patent disclosure as PTX+B=10000).

A is a constant with respect to the mathematical formula for $C_V$ that is determined by trial and error with regard to various different flow rates and different size channels to approximate the real behavior of the flow process, i.e. the drop of the flow when the input pressure is lowered. B is a parameter used for easing the calculations with integers by computer software. This parameter is generally a value of 1 or any multiple thereof, e.g. 10, 100, etc. Thus, as by way of example, if $C_V$ is to be 34.456, it is easier for the processor to calculate the same when utilizing a B value of 1,000 such that $C_V$ is then 34,456.

The calculated coefficient ($C_V$) is characteristic for the specific diameter and condition of endoscope channel and is independent from the variations of working pressure. As noted above, coefficient A is determined from an experimental analysis of the relationship between pressure and flow through a variety of channels.

The following examples serve to illustrate the structure and method for determining whether a particular channel containing medical device such as an endoscope has a leak, is open or blocked and the same serves to illustrate, but not to limit the present invention inasmuch as different structures or methods can also be utilized.

Figure 6:
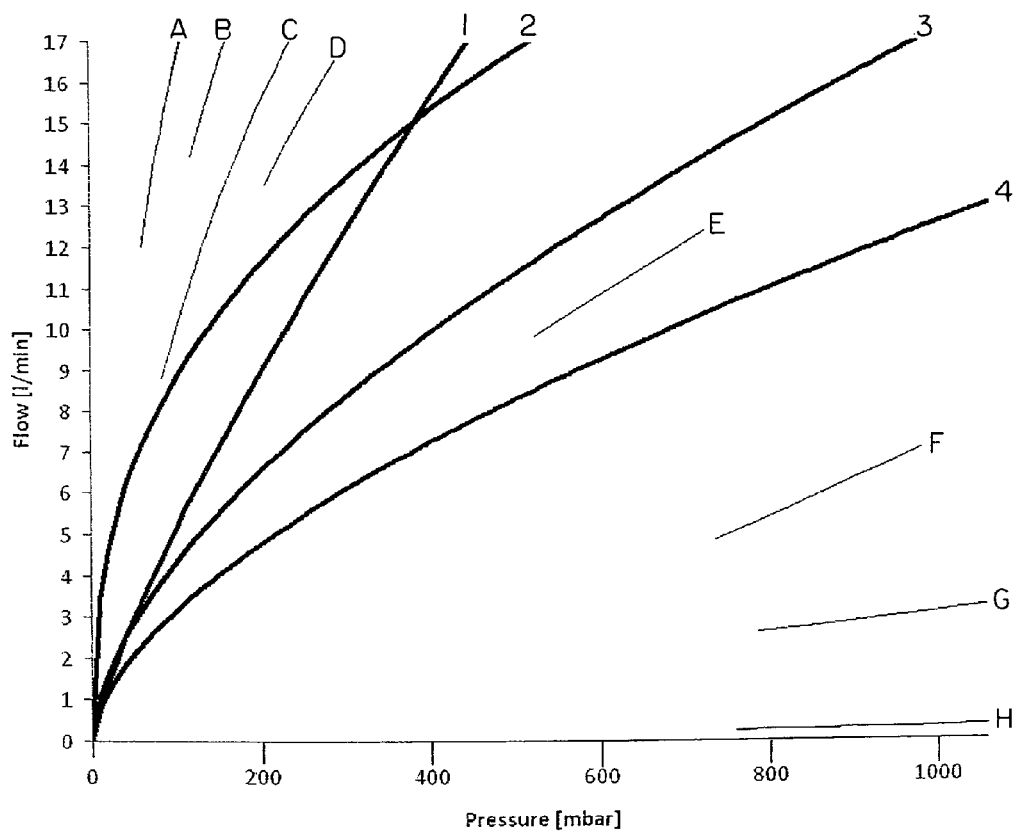
FIG. 6 is an example of a graphical method used to determine the slope and shape of function chart describing relation between pressure and flow.

Procedure:

A procedure for determining an optimized or preferred flow coefficient $C_v$ is as follows:

Point 1. Individual channel containing devices or surrogate device lumens, etc. (65 in FIGS. 1, 3, 4, and 5A) are connected to valve 35 (FIGS. 1, 3, 4, and 5A);

Point 2. Working pressure is set by a precise air pressure regulator 9 (FIGS. 1 and 4) to an initial value (for instance 700 mbar ($7\times10^{-2}$ MPa));

Point 3. The corresponding valve directed to a given channel containing device connected to a given device is opened to allow airflow through the channel containing device;

Point 4. After stabilization of flow, the values of pressure and flow are recorded;

Point 5. The corresponding valve is closed;

Point 6. Working pressure is increased by 100 mbar ($1\times10^{-2}$ MPa);

Point 7. The points 3-6 are repeated until the working pressure has a final determined value (for instance 1,000 mbar ($1.0\times10^{-1}$ MPa);

Point 8. All acquired parameter values analyzed are plotted on a chart that has airflow on a vertical axis and pressure on a horizontal axis as shown in FIG. 6 wherein curves A-H are possible results for various channels—one curve represents results for one channel.

Point 9. Points corresponding to values for individual channels are connected to form a curve;

Point 10. The function $$C_v = \frac{BQ}{P^A}$$

is estimated where: $C_v$=flow value, Q=air flow (liters/min), P=air pressure (mBar), A=an experimental value based pressure/flow exponent (for a given detection system defined in this patent disclosure as PTX+A=0.6), and B=scale coefficient (for a given detection system defined in this patent disclosure as PTX+B=10000).

As noted above, initially B is approximated as being 1 or as indicated in Paragraph [0049] above.

Point 11. Exponent A is optimized, that is changed until the plot of the function has the shape that is the optimal approximation of each of the curves drawn at point 8, i.e. Paragraph [0061]; Then, $C_v$ as shown in the formula is calculated using values of P and Q from measurements made at working pressures of 1000 mbar (Paragraph [0060]), wherein the value of A was estimated as noted above in this paragraph and B=1 ($10^n$ where n=0). Then, the value n of coefficient B is modified ( . . . $10^{-1}$=0.1→$10^0$=1→$10^1$=10→$10^2$=100→ . . . ) so that newly calculated $C_v$ is a number between 1,000 and 10,000. Reference to FIG. 6 shows that the plot changes its shape together with modifications of the two function parameters A. In this paragraph the A is being optimized so that function plot (curves 1-4) have the same shape as the curves plotted from values recoded during practical experiments of Paragraphs [0054-0061](examples shown as curves A-H).

$C_v$ is proportional to the flow velocity (and is "corrected, adjusted" according to actual pressure values). The channel testing device is considered to be blocked (or partially blocked) when $C_v$ is lower than the lower limit. This is because the air flow velocity is much lower, and pressure maintained in the manifold is higher (air does not escape as fast as in case of a channel containing device).

The contrary situation is that when the $C_v$ value is higher than the higher or upper limit, this suggests that the channel containing device is partially or completely detached so there is far less resistance for flowing air and as a result, the value of the pressure maintained in the manifold drops and the value of $C_v$ is high.

The present invention can be adapted for a variety of devices, endoscopes, and instruments. Most flexible endoscopes, as an example, can have the following channels:

1× Suction channel

1× or 2× Biopsy channels

1× Albaran (or Elevator Guide Wire or Raiser Bridge) channel

1×-4× other types of channels (Add Rinse/Water Jet, Air/Water, Air, Lens, Balloon)

Flow coefficients for each individual endoscope and lumen type can vary significantly, but there can be some groups of channel types defined for which the values of the flow coefficient are similar. These are:

Albaran channel

Normal

Biopsy/Suction

Large Biopsy

The system is defined to use as a default setup the Biopsy/Suction range for channels attached to defined connectors within the detecting system (e.g. 1 and 2), and the normal range for all other channels. Some of the channels can be validated using other ranges if additional options are selected or required for the endoscope or other instrument type, see FIG. 7.

Location of Test Apparatus

As previously noted, the various test apparatus embodiments of the present invention can be a separate or stand alone system. Thus, they can be located in any convenient area such as against a wall or on a table as in proximity to a sink for hygiene purposes, e.g., to dispose of waste water or contaminated material leaving the channel containing devices, to clean plugged or partially plugged medical equipment or devices, and the like.

Cleaning of Medical Equipment or Devices

Alternatively, but preferably, the various unblocked lumens can be cleaned of any residue on the internal surfaces thereof by using test apparatus that applies a feedstream mixture containing a cleaning composition such as soap, detergent, surfactant, etc. Examples of such compounds include Prolystica® Ultraconcentrates, Prolystica® Presoak and Cleaner, Klenzyme® detergent, EnzyCare®2 detergent, Hamo™ 100 detergent, and Hamo™ 52 detergent. To aid in a cleaning or scouring effect of the feedstream cleaning mixture, pulsating air can be admitted into the hollow portion of manifold 20 via air flow line 10. Although a cleaning composition can be utilized to initially test each channel containing device with regard to any blockage, it is desirable to apply the cleaning composition after all channel containing devices have been tested.

Exhaust Connectors

Another aspect of the present invention is that exhaust connectors 30 can have permanent openings therein to allow the fluid from manifold 20 to exit therethrough or has openings that can be either open or closed. The purpose of such is to permit controlled leakage of a disinfectant fluid to exit through the connectors and disinfect the same such as between channel containing device test cycles so that subsequently when another channel containing device test is commenced, the connectors are not contaminated and will not contaminate the internal end portion of a channel containing device.

As apparent from the above, the present invention permits monitoring of the flow of a liquid and/or gas through large as well as small channel containing medical devices such as endoscopes, etc. to ensure that flow does occur and also permits automatic verification thereof by a system independent of human intervention. Advantages of the present invention thus include the ability to ensure that a connector providing a flow of gas and/or liquid remains connected to the channel containing medical device to ensure that the device is open during a washing/disinfection process. Another advantage is to be able to ensure proper flow of a gas and/or liquid to various different sizes of channel containing medical devices.

While in accordance with the patent statutes, the best mode and preferred embodiment have been set forth, the scope of the invention is not limited thereto, but rather by the scope of the attached claims.

What is claimed is:

1. An integral apparatus for testing and/or cleaning a channel containing medical device, comprising:
a hollow manifold having at least one exhaust connector, said manifold having at least one pressure sensor for determining the pressure therein, and a solenoid valve located between said exhaust connector and said channel containing device, said solenoid valve operatively connected to said exhaust connector and capable of being operatively connected to said channel containing medical device;
an airflow line having a compressed air source, a pressure switch and a solenoid valve, and an airflow measuring device, said airflow line connected to said manifold, said airflow line capable of maintaining a predetermined pressure;
a microprocessor operatively connected to said airflow line pressure switch, operatively connected to said manifold pressure sensor, operatively connected to said airflow measuring device, operatively connected to said airflow line solenoid valve, and operatively connected to said exhaust connector solenoid valve, and
said microprocessor, upon receiving a signal from said manifold pressure sensor detecting a pressure in said manifold, being capable of energizing said airflow line solenoid valve and also opening said solenoid valve connected to said exhaust connector so that said air in said manifold is capable of flowing into and subsequently out of said channel containing medical device.

2. The apparatus according to claim 1, wherein said airflow line includes a pressure regulator for maintaining said predetermined pressure.

3. The apparatus according to claim 2, wherein said pressure in said airflow line is from 1 to about 5 bars.

4. The apparatus according to claim 2, wherein at least one additional exhaust connector is attached to said hollow manifold, including at least one additional solenoid valve, wherein one of said at least one additional solenoid valve is attached to one of said at least one additional exhaust connector and is capable of being operatively attached to an additional channel containing medical device.

5. The apparatus according to claim 4, including a check valve located between said manifold and said airflow line solenoid valve.

6. The apparatus according to claim 1, wherein the microprocessor compares a predetermined pressure range with a pressure determined by said manifold pressure sensor when said solenoid valve connected to said exhaust connector is open, and wherein a signal is activated when said pressure sensed by said manifold pressure sensor is outside of said predetermined pressure range.

7. The apparatus according to claim 1, wherein a wash connection line is connected to said manifold, wherein a solenoid valve is located on the wash connection line and controls flow of a washing fluid from a wash chamber reservoir into said manifold.

8. The apparatus according to claim 1, wherein pressure in said airflow line ranges from 1 to about 5 bars.

9. The apparatus according to claim 1, wherein a pressure sensor is operatively connected to each exhaust connector, and wherein the microprocessor compares the pressure of said manifold pressure sensor and each exhaust connector sensor that has a channel containing device connected thereto.

10. A method for testing a channel containing medical device, comprising the steps of:
obtaining a testing apparatus comprising a hollow manifold having at least one exhaust connector, a solenoid valve located between said exhaust connector and said channel containing medical device, said solenoid valve operatively attached to said exhaust connector and capable of being attached to said channel containing medical device, said manifold having at least one pressure sensor for determining pressure within the manifold,
said apparatus further including an airflow line having a compressed air source, having a pressure switch, an airflow line solenoid valve and an airflow measuring device, said airflow line operatively connected to said manifold,
said testing apparatus further including a microprocessor operatively connected to said pressure switch of said airflow line, to said airflow line solenoid valve, to said manifold pressure sensor, to said exhaust connector solenoid valve, and operatively connected to said airflow measuring device;
operatively connecting said connector solenoid valve to said channel containing medical device; and
opening said airflow line solenoid valve and determining the pressure in said manifold with said manifold pressure sensor.

11. The method according to claim 10, wherein the apparatus provides a signal when said manifold pressure exceeds a preselected pressure value or falls below said pre-selected pressure value.

12. The method according to claim 11, wherein a check valve is located between said manifold and said solenoid valve of said airflow line.

13. The method according to claim 12, wherein said airflow line includes a pressure regulator for maintaining a predetermined pressure in said manifold before said exhaust connector solenoid valve is opened, and wherein said airflow line pressure is from 1 to about 5 bars.

14. The method according to claim 13, wherein a washing connection line is connected to said manifold, wherein a solenoid valve is located on said washing connection line and controls entrance of a washing fluid from a wash chamber reservoir into said manifold.

15. The method according to claim 10, wherein pressure in said airflow line ranges from 1 to about 5 bars.

16. The method according to claim 10, wherein a pressure sensor is operatively connected to said exhaust connector, and wherein the microprocessor compares the pressure between said manifold pressure sensor and said exhaust connector sensor.

17. An integral apparatus for testing and/or cleaning a channel containing medical device, comprising:

a hollow manifold having at least one exhaust connector, a solenoid valve located between said exhaust connector and said channel containing medical device, said solenoid valve operatively connected to exhaust connector and capable of being operatively connected to said channel containing medical device, said manifold having at least one pressure sensor for determining the pressure therein;

an airflow line having a compressed air source, having a pressure switch and a solenoid valve, said airflow line capable of maintaining a predetermined pressure, said airflow line connected to said manifold, and said airflow line having an airflow measuring device;

a microprocessor operatively connected to said airflow line pressure switch, said microprocessor also being operatively connected to said manifold pressure sensor and operatively connected to said airflow line solenoid valve, and operatively connected to said airflow measuring device;

said microprocessor, upon receiving a signal from said manifold pressure sensor detecting a pressure in said manifold, being capable of energizing said airflow line solenoid valve and also opening said solenoid valve connected to said exhaust connector so that said air in said manifold is capable of flowing into said channel containing medical device.

18. The apparatus according to claim 17, wherein said airflow line includes a pressure regulator for maintaining said predetermined pressure, and wherein said microprocessor is operatively connected to said airflow measuring device.

19. The apparatus according to claim 18, wherein at least one additional exhaust connector is attached to said hollow manifold, including at least one additional solenoid valve, wherein one of said at least one additional solenoid valve is attached to one of said at least one additional exhaust connector and is capable of being operatively attached to an additional channel containing medical device, and including a check valve located between said manifold and said airflow line solenoid valve.

* * * * *